(12) United States Patent
Hillhouse et al.

(10) Patent No.: US 8,080,483 B2
(45) Date of Patent: Dec. 20, 2011

(54) DOUBLE GYROID STRUCTURE NANOPOROUS FILMS AND NANOWIRE NETWORKS

(75) Inventors: Hugh W. Hillhouse, West Lafayette, IN (US); Vikrant N. Urade, Karnataka (IN); Ta-Chen Wei, Newark, DE (US); Michael P. Tate, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 1083 days.

(21) Appl. No.: 11/933,494

(22) Filed: Nov. 1, 2007

(65) Prior Publication Data
US 2011/0278533 A1    Nov. 17, 2011

Related U.S. Application Data

(60) Provisional application No. 60/921,967, filed on Apr. 5, 2007.

(51) Int. Cl.
*H01L 21/469*   (2006.01)
*H01L 21/31*    (2006.01)

(52) U.S. Cl. ........ 438/780; 438/758; 438/781; 438/782; 438/784; 438/778; 257/E21.012; 257/E21.013; 257/E21.151; 257/E21.273

(58) Field of Classification Search ........... 257/E21.012, 257/E21.013, E21.151, E21.273
See application file for complete search history.

(56) References Cited

U.S. PATENT DOCUMENTS

| 7,794,828 | B1 * | 9/2010 | Momoda et al. | 428/307.7 |
| 2006/0040507 | A1 * | 2/2006 | Mak et al. | 438/758 |
| 2006/0084282 | A1 * | 4/2006 | Dubois et al. | 438/781 |
| 2007/0141854 | A1 * | 6/2007 | Chao et al. | 438/758 |

OTHER PUBLICATIONS

Hideki Masuda et al., entitled "Ordered Metal Nanohole Arrays Made by a Two-Step Replication of Honeycomb Structures of Anodic Alumina," Science, vol. 268, No. 5216, Jun. 9, 1995, pp. 1466-1468.
T. Thurn-Albrecht et al., entitled "Nanoscopic Templates from Oriented Block Copolymer Films," Advanced Materials, vol. 12, No. 11, Jun. 2, 2000, pp. 787-791.
Alan H. Schoen, entitled "Infinite Periodic Minimal Surfaces Without Self-Intersections," NASA Technical Note, NASA TN D-5541, May 1970, pp. 1-93 (including, beginning pp. i-vii).
Frank S. Bates et al., entitled "Block Copolymers-Designer Soft Materials," Physics Today, Feb. 1999, pp. 32-38.
J.S. Beck et al., entitled "A New Family of Mesoporous Molecular Sieves Prepared with Liquid Crystal Templates," Journal of the American Chemical Society, vol. 114, No. 27, Dec. 30, 1992, pp. 10834-10843.

(Continued)

*Primary Examiner* — Mohsen Ahmadi
(74) *Attorney, Agent, or Firm* — Brinks Hofer Gilson & Lione

(57) ABSTRACT

A method of forming a nanoporous film is disclosed. The method comprises forming a coating solution including clusters, surfactant molecules, a solvent, and one of an acid catalyst and a base catalyst. The clusters comprise inorganic groups. The method further comprises aging the coating solution for a time period to select a predetermined phase that will self-assemble and applying the coating solution on a substrate. The method further comprises evaporating the solvent from the coating solution and removing the surfactant molecules to yield the nanoporous film.

12 Claims, 10 Drawing Sheets

OTHER PUBLICATIONS

Tae-Wan Kim et al., entitled "MCM-48-like Large Mesoporous Silicas with Tailored Pore Structure: Facile Synthesis Domain in a Ternary Triblock Copolymer-Butanol-Water System," Journal of the American Chemical Society, vol. 127, No. 20, May 25, 2005, pp. 7601-7610.

C. Jeffrey Brinker et al., entitled "Evaporation-Induced Self-Assembly: Nanostructures Made Easy," Advanced Materials, vol. 11, No. 7, May 7, 1999, pp. 579-585.

Vanessa Z.-H. Chan et al., entitled "Ordered Bicontinuous Nanoporous and Nanorelief Ceramic Films from Self Assembling Polymer Precursors," Science, vol. 286, No. 5445, Nov. 26, 1999, pp. 1716-1719.

Ryan C. Hayward et al., entitled "Thin Films of Bicontinuous Cubic Mesostructured Silica Templated by a Nonionic Surfactant," Langmuir, vol. 20, No. 14, Jul. 6, 2004, pp. 5998-6004.

Michaela Klotz et al., entitled "Synthesis conditions for hexagonal mesoporous silica layers," Journal of Materials Chemistry, vol. 10, No. 1-4, 2000, pp. 663-669.

David Grosso et al., entitled An in Situ Study of Mesostructures CTAB—Silica Film Formation during Dip Coating Using Time-Resolved SAXS and Interferometry Measurements, Chemistry of Materials, vol. 14, No. 2, Feb. 2002, pp. 931-939.

Florence Cagnol et al., entitled "Humidity-controlled mesostructuration in CTAB-templated silica thin film processing. The existence of a modulable steady state," Journal of Materials Chemistry, vol. 13, No. 1, Jan. 2003, pp. 61-66.

D. Grosso et al., entitled "Fundamentals of Mesostructuring Through Evaporation-Induced Self-Assembly," Advanced Functional Materials, vol. 14, No. 4, Apr. 2004, pp. 309-322.

M. P. Tate et al., *Journal of Physical Chemistry B Accepted*. (2006).

Piotr Garstecki et al., entitled "Scattering Patterns of Multiply Continuous Cubic Phases in Block Copolymers. I. The Model," Macromolecules, vol. 36, No. 24, Dec. 2, 2003, pp. 9181-9190.

H.G. von Schnering et al., entitled "Nodal surfaces of Fourier series: fundamental invariants of structured matter," Condensed Matter, vol. 83, No. 3, 1991, pp. 407-412.

Leonid A. Solovyov et al., entitled "X-ray Diffraction Structure Analysis of MCM-48 Mesoporous Silica," The Journal of Physical Chemistry B, vol. 109, No. 8, Mar. 3, 2005, pp. 3233-3237.

Yasuhiro Sakamoto et al., entitled "Three-Dimensional Structure of Large-Pore Mesoporous Cubic *Ia3d* Silica with Complementary Pores and Its Carbon Replica by Electron Crystallography," Angewandte Chemie International Edition, vol. 43, No. 39, Oct. 4, 2004, pp. 5231-5234.

Chaojie Song et al., entitled "Electrode modification with spin-coated films of mesoporous molecular sieve silicas," Microporous and Mesoporous Materials, vol. 44-45, Jun. 2001, pp. 679-689.

Nanguo Liu et al., entitled "Photoregulation of Mass Transport through a Photoresponsive Azobenzene-Modified Nanoporous Membrane," Nano Letters, vol. 4, No. 4, Apr. 2004, pp. 551-554.

Mathieu Etienne et al., entitled "Evaporation induced self-assembly of templated silica and organosilica thin films on various electrode surfaces," Electrochemistry Communications, vol. 7, No. 12, Dec. 2005, pp. 1449-1456.

Dina Fattakhova Rohlfing et al., entitled Functionalized Mesoporous Silica Films as a Matrix for Anchoring Electrochemically Active Guests, Langmuir, vol. 21, No. 24, Nov. 22, 2005, pp. 11320-11329.

C. Amatore et al., entitled "Charge Transfer at Partially Blocked Surfaces, a Model for the Case of Microscopic Active and Inactive Sites," Journal of Electroanalytical Chemistry and Interfacial Electrochemistry, vol. 147, 1983, pp. 39-51.

Eyal Sabatani et al., entitled "Thioaromatic Monolayers on Gold: A New Family of Self-Assembling Monolayers," Langmuir, vol. 9, No. 11, Nov. 1993, pp. 2974-2981.

Richard P. Janek et al., entitled "Impedance Spectroscopy of Self-Assembled Monolayers on Au(111): Sodium Ferrocyanide Charge Transfer at Modified Electrodes," Langmuir, vol. 14, No. 7-11, 1998, pp. 3011-3018.

A. J. Bard, L. R. Faulkner, Electrochemical Methods, (Wiley, 2001).

E. Barsoukov, J. R. Macdonald, *Impedance spectroscopy: theory, experiment, and applications*, Wiley-Interscience, 2005).

Brian W. Eggiman et al., entitled "Rhombohedral Structure of Highly Ordered and Oriented Self-Assembled Nanoporous Silica Thin Films," Chemistry of Materials, vol. 18, No. 3, Feb. 7, 2006, pp. 723-730.

Michael P. Tate et al., entitled "Order and Orientation Control of Mesoporous Silica Films on Conducting Gold Substrates Formed by Dip-Coating and Self Assembly: A Grazing Angle of Incidence Small-Angle X-ray Scattering and Field Emission Scanning Electron Microscopy Study," Langmuir, vol. 21, No. 22, Oct. 25, 2005, pp. 10112-10118.

Yasuhiro Sakamoto et al., entitled "Direct Imaging of the Pores and Cages of Three-Dimensional Mesoporous Materials," Nature, vol. 408, No. 6811, Nov. 23, 2000, pp. 449-453.

Freddy Kleitz et al., entitled "Large Cage Face-Centered-Cubic *Fm3m* Mesoporous Silica: Synthesis and Structure," The Journal of Physical Chemistry, vol. 107, No. 51, Dec. 25, 2003, pp. 14296-14300.

Donghai Wang et al., entitled "Electrodeposition of Metallic Nanowire Thin Films Using Mesoporous Silica Templates," Advanced Materials, vol. 15, No. 2, Jan. 16, 2003, pp. 130-133.

Donghai Wang et al., entitled "A General Route to Macroscopic Hierarchical 3D Nanowire Networks," Angewandte Chemie-International Edition, vol. 43, No. 45, Dec. 1, 2004, pp. 6169-6173.

Jinlou Gu et al., entitled "Periodic Pulse Electrodeposition to Synthesize Ultra-high Density CdS Nanowire Arrays Templated by SBA-15 Mesoporous Films," Chemistry Letters, vol. 33, No. 7, Jul. 5, 2004, pp. 828-829.

Hongmei Luo et al., entitled "Magnetic Cobalt Nanowire Thin Films," The Journal of Physical Chemistry B, vol. 109, No. 5, Feb. 10, 2005, pp. 1919-1922.

Keying Shi et al., entitled "Porous Crystalline Iron Oxide Thin Films Templated by Mesoporous Silica," Microporous and Mesoporous Materials, vol. 83, 2005, pp. 219-224.

Donghai Wang et al., entitled "Templated Synthesis, Characterization, and Sensing Application of Macroscopic Platinum Nanowire Network Electrodes," Journal of Nanoscience and Nanotechnology, vol. 5, No. 11, Nov. 2005, pp. 1904-1909.

Mizue Kaneda et al., entitled "Structural Study of Mesoporous MCM-48 and Carbon Networks Synthesized in the Spaces of MCM-48 by Electron Crystallography," The Journal of Physical Chemistry, vol. 106, No. 6, Feb. 14, 2002, pp. 1256-1266.

* cited by examiner

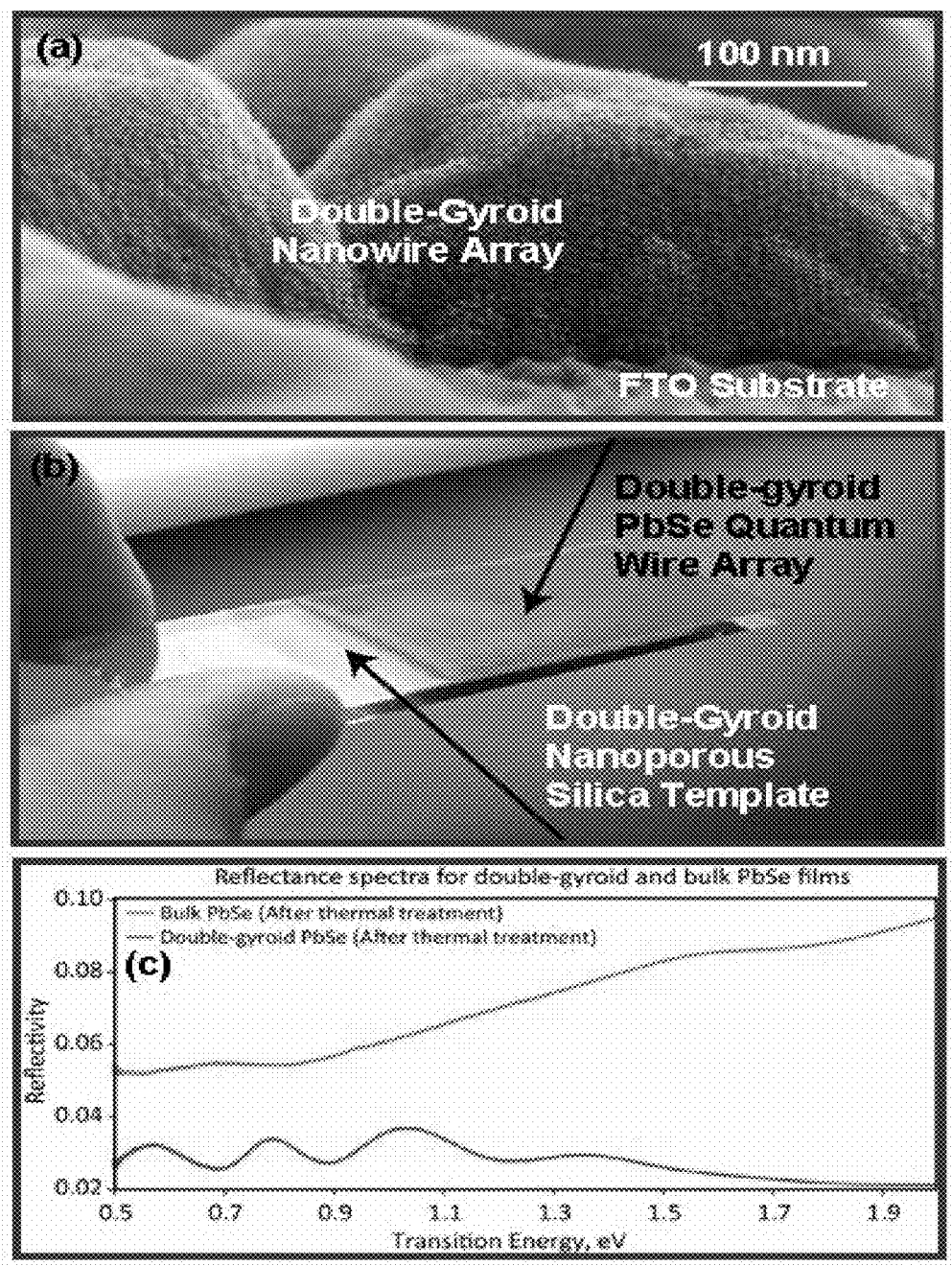
Fig. 10 (a)-(c)

DOUBLE GYROID STRUCTURE NANOPOROUS FILMS AND NANOWIRE NETWORKS

CROSS-REFERENCE TO RELATED APPLICATION

This application claims the benefit of U.S. Provisional Application No. 60/921,967, filed on Apr. 5, 2007, entitled "DOUBLE GYROID STRUCTURE NANOPOROUS FILMS AND NANOWIRE NETWORKS," the entire contents of which are incorporated herein by reference.

This invention was made in part with government support from CAREER Award No. 0134255-CTS awarded by the National Science Foundation ("NSF"). The Government has or may have certain rights in the invention.

TECHNICAL FIELD

The present invention generally relates to porous films where the pore sizes are controlled by a process of self-assembly. The pores are on the nanometer length scale, and the films are referred to as nanoporous or mesoporous. In particular, the invention relates to nanoporous films and their use in forming nanowires that are interconnected in three dimensions to yield a periodic network that is derived from a double-gyroid topology.

BACKGROUND OF THE INVENTION

Highly ordered nanoporous films that provide accessibility to an underlying substrate are a key cornerstone of nanofabrication. Bottom-up fabrication technologies based on both anodic oxidation of aluminum and orienting assembled block copolymers have advanced rapidly and are now widely used to generate films with controlled pore sizes below 50 nm that directly access the substrate. However, for pores in the 1-10 nm range, similar milestones have not been reached, and there are no bottom-up technologies that provide well-defined periodic access to a substrate at this length scale without also yielding cracks or access through larger openings. 1-10 nm is an important size range though since the surface area increases dramatically as pore size decreases (at constant void fraction) and many quantum size effects are only observed when the length scale is less than the thermal de Broglie wavelength (which is typically less than 10 nm). As a result developing nanoporous films with smaller pores that access the substrate are important for the development of high sensitivity sensors, high surface area electrodes for fuel cells or photoelectrochemical devices, and nanostructured thermoelectrics or photovoltaics.

Nanofabrication by electrochemical deposition in an ordered porous template can be used to generate new materials for the devices above. However, this technique requires that solution phase species are able to access the substrate and transfer electrons. One way to generate this access is to self-assemble a 3D nanostructure based on a low interfacial curvature phase. One such nanostructure is the phase based on the gyroid minimum surface. This zero mean curvature surface divides space into two continuous, non-intersecting domains. When a wall replaces the gyroid surface, a tricontinuous structure results (one wall and two pore systems). Tricontinuous gyroid structures are actually quite common in block copolymer systems and typically occur between the lamellar and cylindrical phases on the spectrum of interfacial curvature. (It should be noted that there may some microporosity in the wall that connects the two pore systems. Regardless of this, the films are still referred to as "tricontinuous"). However, the synthesis of nanoporous gyroid structures in thin film morphology with small pore sizes has proven very challenging.

BRIEF SUMMARY OF THE INVENTION

The present teachings are directed to highly ordered nanoporous films with a structure based on the gyroid minimum surface and the use of these films to template other materials. The nanoporous films are formed by self-assembly of inorganic species and surfactant molecules using a new approach that yields coating solutions that are stable for months and may be used over a broad range of temperature and relative humidity (spanning normal laboratory conditions) from commercially available surfactants. This new approach differs from previous art in many ways including the use of aging (prior to coating) to control the phase that self-assembles. After self-assembly and consolidation of the inorganic material, the surfactant molecules are removed by calcination, solvent extraction, ozone treatment, or plasma treatment to yield nanoporous films. These nanoporous films are then used as a template by filling the pore system with another material. The structures may be used as is, or the original inorganic material may be removed to yield a new nanoporous film. In exemplary embodiments, the tricontinuous films synthesized on conducting electrodes are composed of one continuous dense silica wall approximately 4.6 nm thick and two continuous but non-intersecting pore systems with characteristic pore diameter of approximately 4.3 nm. Moreover, the void fraction and surface area are approximately 0.48 and 477 $m^2/g$, respectively. Electrochemical impedance spectroscopy is used to quantitatively determine the diffusion coefficient in the film and the percentage of the substrate that is accessible to electrochemical probe molecules when the walls are at their isoelectric point. The values for accessibility obtained electrochemically (31%±3%) matches well the value obtained from the model of the nanoporous film reconstructed from GISAXS, FESEM and TEM data (31%). Additionally, the liquid phase diffusion coefficient of a molecule in the water filled film is measured to be 0.44 times the diffusion coefficient in bulk liquid. This shows the dramatic difference in accessibility and mass transport when compared to other nanoporous films.

According to one exemplary illustration, highly ordered and oriented nanoporous silica films based on 3D face-centered cubic or 2D hexagonal nanostructures are measured by the same method to have accessible areas less than 0.02% and diffusion coefficients less than 0.01 time the diffusion coefficient in bulk liquid. Platinum nanowire films are then fabricated by electrochemical deposition to fill the two pore systems followed by an etching step to remove the silica. The local and long-range order of the nanowire network is retained from the silica template and results in replication of the nanopore network with high fidelity. These new nanoporous silica film coated electrodes and platinum nanowire electrodes should be of immediate interest for electrochemical sensors, fuel cell electrodes, and photoelectrochemical devices. In addition, these films open up a general route for nanofabrication of ordered structures on the sub-10 nm length scale yielding a route to nanostructured thermoelectrics and photovoltaics that utilize quantum confinement.

The present teachings involve a convenient and reproducible, room temperature synthesis of tricontinuous silica films from commercially available templates that yield an accessible area of the substrate through the well-defined mesopores. In certain exemplary embodiments, the pore network comprises two mesopore networks separated by a microporous inorganic wall. In one exemplary embodiment at least about 25% of the substrate is accessible through the mesopores. In further exemplary embodiments, at least about 30% of the substrate is available through the mesopores. In yet further exemplary embodiments, at least about 31% of the substrate is available through the mesopores. In still further exemplary embodiments, at least about 50% of the substrate is available through the mesopores. It is believed that this is the first room temperature synthesis of gyroid-based silica films with pores less than about 10 nm and the first quantitative and accurate measurement of substrate accessibility for self-assembled silica films. This facile accessibility is exploited to electrodeposit platinum in the pore structure to yield highly ordered platinum nanowire networks. According to one exemplary embodiment, the rate of filling the pore network is at least about 30% as fast as electrodepositing onto a substrate as if no silica film were present. According to another exemplary embodiment, the rate of filling the pore network is at least about 50% as fast as electrodepositing onto a substrate as if no silica film were present. In additional exemplary embodiments, the rate of filling the pore network is at least about 70% as fast as electrodepositing onto a substrate as if no silica film were present. In still further exemplary embodiments, the rate of filling the pore network is at least about 90% as fast as electrodepositing onto a substrate as if no silica film were present. While this is the first report of electrodeposition in a gyroid-based structure, it is also the first report of any sub-10 nm diameter nanowire network with long-range order.

In one example, the present invention provides a method of forming a nanoporous film. The method comprises forming a coating solution including inorganic clusters, surfactant molecules, and a solvent and then aging the coating solution for a predetermined time period to control the phase that will self-assemble under a given set of environmental conditions. The method further comprises applying the coating solution on a substrate and evaporating the solvent from the coating solution. The method further comprises removing the surfactant molecules to yield the nanoporous film. In certain exemplary illustrations according to this embodiment, the coating solution is aged for a time period (prior to the coating process) that is selected to correspond to a desired interfacial curvature of the nanoporous film. In specific exemplary embodiments, the inorganic clusters are comprised of silicon and oxygen to yield silica nanoporous films. In further specific exemplary embodiments, the inorganic clusters are formed from the hydrolysis of a silicon alkoxide, such as tetraethylorthosilicate. In further specific exemplary embodiments, the clusters are organic-inorganic species consisting formed from the hydrolysis of a silicon alkoxide, such as tetraethylorthosilicate.

In another example, the present invention provides a nanoporous structure. The nanoporous structure comprises a substrate and a nanoporous film deposited on the substrate. The film defines a pore network having pores with an average size of less than about 10 nm, wherein at least about 25% of the substrate is accessible through the pore network at the substrate-film interface.

In further exemplary embodiments according to the present teachings, the pore network is comprised of pores with an average size of less than about 5 nm.

BRIEF DESCRIPTION OF THE DRAWINGS

The above-mentioned aspects of the present teachings and the manner of obtaining them will become more apparent and the teachings will be better understood by reference to the following description of the embodiments taken in conjunction with the accompanying drawings, wherein:

FIG. 10(a) depicts a photograph of a nanoporous film that has been electrochemically filled with PbSe. The PbSe nanowires have the same structure as the platinum wires in FIG. 5.

FIG. 10(b) depicts the reflectance spectra of the PbSe nanowires and shows oscillations due to quantum confinement.

FIG. 10(c) depicts reflectivity data showing oscillations due to quantum confinement.

Corresponding reference characters indicate corresponding parts throughout the several views.

DETAILED DESCRIPTION OF THE INVENTION

Figure 1:
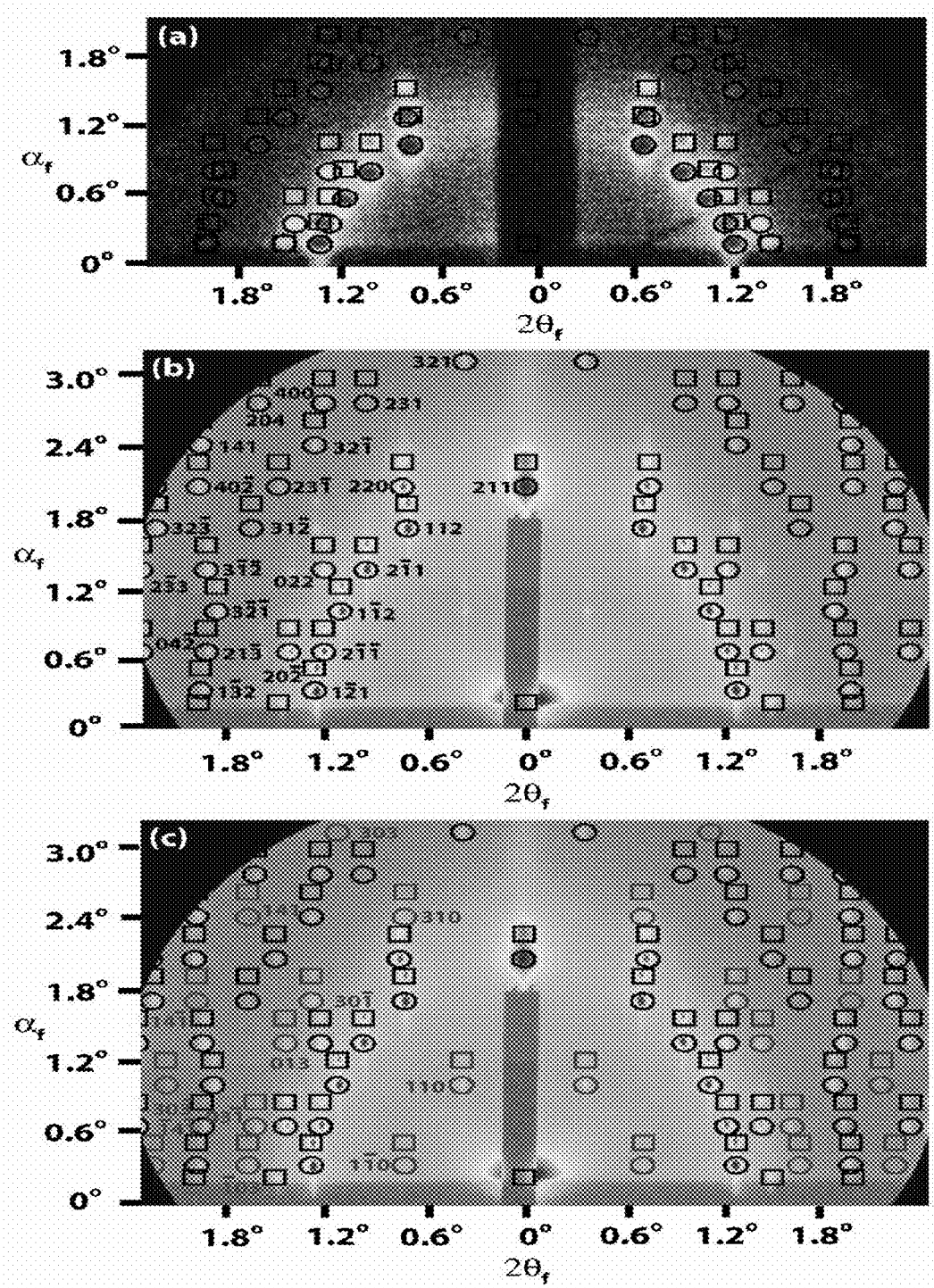
FIGS. 1a-c depict GISAXS patterns of nanostructured tricontinuous films before and after copolymer removal with overlays of predicted positions of diffraction spots calculated under the DWBA using NANOCELL.

The embodiments of the present teachings described below are not intended to be exhaustive or to limit the teachings to the precise forms disclosed in the following detailed description. Rather, the embodiments are chosen and described so that others skilled in the art may appreciate and understand the principles and practices of the present teachings.

Robust Synthesis of Tricontinuous-Phase NanoDorous Films

In the evaporation induced self-assembly (EISA) synthesis of nanoporous films discussed here, the coating solution contains an inorganic or inorganic-organic precursor species that may undergo hydrolysis, condensation, and/or protonation/deprotonation reactions. As a result, the precursor molecules exist as single molecules or as clusters that evolve with aging time prior to coating. In one exemplary embodiment, the precursor is the silicon alkoxide species called tetraethylorthosilicate (TEOS). In this example the clusters are built from a silicon atom with any mixture of the following groups attached: —OH, —OH$_2^+$, —O$^-$, —OCH2CH3, —O—Si≡.

In another exemplary embodiment, the precursor is an organosilica bridge silesquioxane species called 1,2-bis(triethoxysilyl)ethane (BTESE). In this example, the clusters are built from a core of ≡Si—C—C—Si≡ with any of the following groups attached: —OH, —OH2$^+$, —O$^-$, —OCH2CH3, ≡Si—C—C—Si≡). As a result changes in coating solution with aging time, there is typically a window of time over which EISA yields an ordered nanostructure that depends on the coating solution composition (for example the pH and hydrolysis ratio). The coating solutions are then applied by dip-coating or spin-coating to form a thin liquid film on a substrate. Other liquid coating techniques such as spray-coating, roll coating, or knife coating may be used as well. After coating, the vapor-phase composition (humidity and the presence of other solvents) plays a key role in determining the interfacial curvature of the nanostructure. For CTAB templated silica films aging time primarily affects the degree of ordering. However, as shown by the present teachings, for films templated by surfactants containing poly(ethylene oxide) as the hydrophilic component, aging of the coating solution provides a means to precisely and subtly control interfacial curvature.

In one exemplary embodiment this approach is used to synthesize nanoporous films with the double gyroid structure from an alkane-modified poly(ethylene oxide)-poly(propylene oxide) surfactant that displays a region of cubic phase stability in its aqueous phase diagram at compositions between the 2D hexagonal and lamellar phases (about 62-66 wt % copolymer for $EO_{17}$-$PO_{12}$-$C_{14}$ at room temperature). After mixing the coating solution, films formed by EISA show a systematic progression from high to low curvature silica nanostructures with increasing aging time of the coating solution (3D packing of spherical silica/micelle structures→2D packing of cylindrical silica/micelle structures→tricontinuous (double gyroid) structure→lamellar). After 10 days of aging at room temperature, high-quality pure tricontinuous-phase nanostructured films self-assemble when dip-coated. The time window where good quality films may be dip-coated extends up to about 30 days when the coating solution is stored at room temperature. However, if the coating solution is refrigerated after about 10 days of aging at room temperature, consistently high-quality nanoporous silica films with the tricontinuous structure are obtained even after 3 months of storage and even when dip-coated over a broad range of relative humidity (between about 25% and 75%). If the amount of water added to make the coating solution changes, the optimum aging time changes. Also, if the temperature at which the solution is aged changes, the optimum aging time also changes. The optimum aging time can be shift to times shorter than 6 hours as well as times exceeding about 30 days.

In another exemplary embodiment Pluronic P84 was used as the templating surfactant molecule (instead of the $EO_{17}$-$PO_{12}$-$C_{14}$). P84 has a formula of approximately $EO_{19}$-$PO_{43}$-$EO_{19}$. The same phenomena with aging are observed Film Structure, Order, and Orientation In one exemplary illustration according to the present teachings, grazing-angle-of-incidence small-angle x-ray scattering (GISAXS) is used to assess the symmetry and order in the films. The GISAXS patterns are interpreted using the Distorted Wave Born Approximation (DWBA) to calculate the positions of the Bragg diffraction spots, including the effects of refraction and reflection (FIG. 1). According to this exemplary illustration, the Bragg spots of the as-synthesized film can be accurately described by a gyroid cubic structure that is highly oriented with its 211 planes parallel to the substrate and has undergone a 7% contraction perpendicular to the substrate. The (211) oriented domains span the thickness of the film and extend laterally several microns. Despite the fact cubic symmetry is broken, the systematic absences are still explained by the gyroid extinction conditions (space group Ia-3d) since the distribution of electron density still possesses this symmetry. After copolymer removal by calcination, the extent of unidirectional contraction increases to about 40%. The main features of the GISAXS pattern are still well-described by the systematic absences of the double gyroid structure (FIG. 1b). However, smaller intensity peaks do appear and can be used to identify which symmetry elements are broken. These broken symmetries are b and c glide planes parallel to the (100) of the uncontracted cubic structure; the c and a glide planes parallel to the (010); the d glide planes parallel to the (1-10) and (110); and the d glide planes parallel to the (-101) and (101). These relax the extinction conditions 0kl (for k,l=2n); h0l (for h,l=2n); hhl and h-hl (for 2 h+l=4n); and hkh and -hkh (for 2h+k=4n), respectively. Here it should be noted that in bicontinuous gyroid structures where one of the two enantiomeric continuous regions is filled and the other continuous region is empty (the pore system), the structure has $I4_132$ symmetry which would yield additional peaks not observed here. This suggests that the nanoporous silica films have a tricontinuous structure—two individually continuous pore systems separated by a nonporous inorganic wall, such as a continuous silica wall that is based on a uniaxially contracted gyroid minimum surface.

Figure 2:
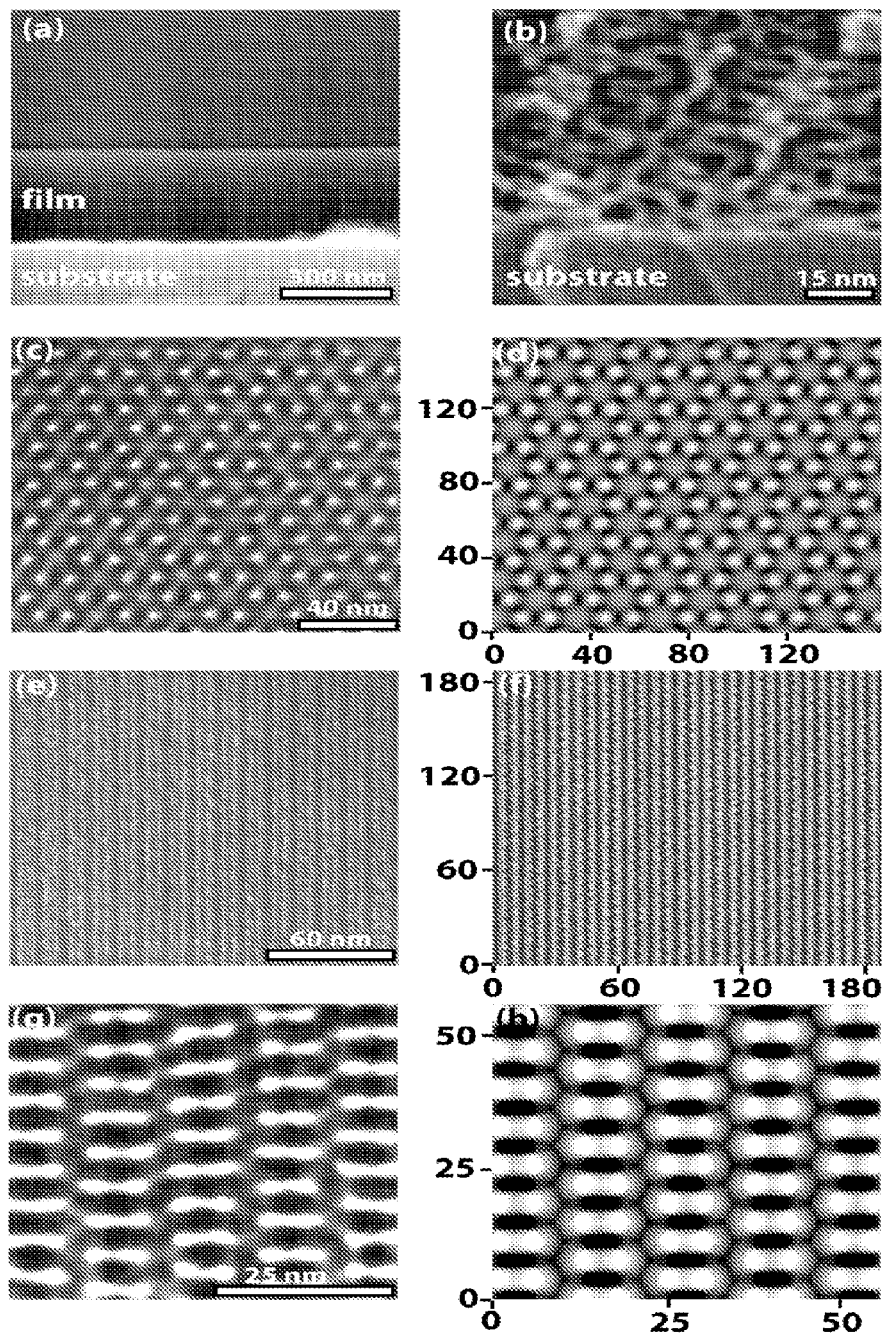
FIGS. 2a-h depict experimental and simulated TEM images of nanoporous films.

The structure and topology were examined by FESEM and TEM (FIG. 2). Experimental TEM images were compared with projections of electron density calculated from several possible structures that are based on the gyroid minimum surface. An excellent match was found between the observed TEM images and those simulated from a tricontinuous structure where the gyroid minimal surface runs down the center of a silica wall separating the two pore systems. The uncontracted cubic structure was generated by assuming a constant wall thickness (t) and placing electron density in regions of space defined by a constant level of the periodic nodal surface given in terms of wall thickness by:

$$\left| \sin\left(\frac{2\pi x}{a}\right)\cos\left(\frac{2\pi y}{a}\right) + \sin\left(\frac{2\pi y}{a}\right)\cos\left(\frac{2\pi z}{a}\right) + \sin\left(\frac{2\pi z}{a}\right)\cos\left(\frac{2\pi x}{a}\right) \right| \leq \frac{\sqrt{3}}{2}\sin\frac{2\pi t}{\sqrt{3}\,a}$$

where a is the lattice constant of the uncontracted cubic structure (determined from GISAXS of planes perpendicular to the substrate to be 17.9 nm). This structure was then oriented such that the (211) planes were parallel to the substrate and then uniaxially contracted towards the substrate by applying rotation and deformation matrices. Due to the contraction, the wall thickness of the contracted structure is not constant, and varies systematically from about 3.4 nm to about 5.7 nm, with an average of about 4.6 nm (commensurate with FESEM data). The projected electron densities along any given [hkl] direction were then calculated by integration. A Gaussian blur was applied to the projected density to account for aberration in the imaging process.

Figure 3:
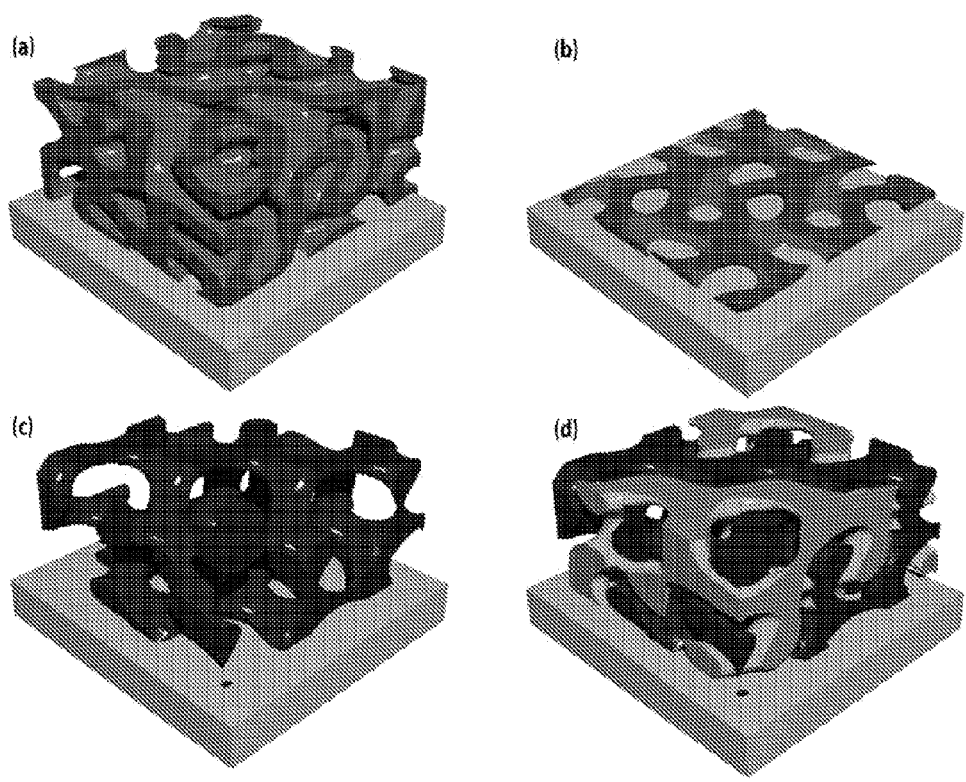
FIGS. 3a-d depict three dimensional rendering of contracted tricontinuous nanoporous films reconstructed from GISAXS, TEM, and FESEM.

Determination of the lattice constants and orientation from GISAXS, the topology from TEM imaging and simulation, and the wall thickness from FESEM imaging allows the reconstruction of a low resolution 3D model of the structure (FIG. 3). The volume void fraction and mesopore surface area were calculated numerically from the 3D reconstruction of the film to be about 0.48 cm$^3_{pore}$/cm$^3_{film}$ and about 5.82×10$^6$ cm$^2_{surface}$/cm$^3_{film}$. Also, the critical angle for x-ray scattering for the calcined nanoporous film was measured by GISAXS to be about 0.165°. The average electron density of the calcined film is then calculated from the critical angle to be about 347 electrons/nm$^3$. The density of the silica wall may then be calculated from the electron density and void fraction and is found to be about 2.24 g/cm$^3$. This corresponds closely to the value of dense amorphous silica and suggests that there is little microporosity in the wall (however, this should be confirmed by a higher resolution technique). From these parameters, the internal mesopore surface area and mesopore volume of the contracted film are calculated to be about 477 m$^2$/g and about 0.56 cm$^3$/g. For comparison, a 2D hexagonal silica phase with the same minimum wall thickness and pore diameter (about 3.4 nm and about 4.3 nm) has an internal mesopore surface area and mesopore volume of about 81 m$^2$/g and about 0.17 cm$^3$/g, respectively. It was recently suggested on the basis of HRTEM and electron crystallography that the two continuous pore systems (for gyroid structure nanoporous silica powders) may be interconnected by a small pore through the silica wall at the 16a site. However, the resolution of the reconstruction reported here is too low to determine if similar structural phenomena occur in the film morphology.

The planar void fraction for any slice of the tricontinuous nanostructure may also be calculated from the reconstructed model. Both the minimum and maximum planar void fractions occur for slices parallel to the (211) planes, ranging from about 0.31 to about 0.63. The slice with the lowest planar void fraction (highest fraction of silica) should be the most hydrophilic while the highest planar void fraction should be the most hydrophobic. This explains why the films are (211) oriented. Further, it is hypothesized that the slice parallel to the (211) with the highest planar density of silica will be the slice in contact with the substrate (since the substrate is hydrophilic), and will thus determine the footprint the film leaves on the electrode and determine the fraction of accessible substrate area. The footprint that results from this slice is shown in FIG. 3b.

Electrochemically Accessible Substrate Area

The accessibility of the pore volume in nanoporous powders is typically determined using nitrogen adsorption. However, this technique is not capable of giving any direct indication of accessibility to the substrate underlying a nanoporous film. Also, due to solvation and surface charge effects, the accessibility of the substrate to a solution phase species can be vastly different from the accessibility of a gas phase species. Electrochemical techniques may be used to address this question, but care must be taken to calculate accurate values of the accessible area. There have been only a few electrochemical studies that involve self-assembled continuous nanoporous film coated electrodes. However, only one reports a quantitative measure of the accessible substrate area. It is believed that about 70% of the substrate is electrochemically accessible by comparing the peak currents from cyclic voltammetry (CV) of coated and bare electrodes. However, this method is accurate only when the diffusion layer thickness ($\delta$) is much smaller than the length scale of active regions of the electrode ($d_a$). When $\delta$ is on the order of $d_a$ but smaller than the distance of separation between active patches ($d_s$), it yields values of accessible area that are artificially high, due to the increased current from 3D diffusion at the edges of the active regions. However, when $\delta \gg d_a$ and $\delta \gg d_s$, as is the case for surfactant templated nanoporous films, this method may over estimate of the accessible surface area.

Under these conditions the area that contributes to the peak current in CV is the geometric area, and increasing the fraction of the electrode surface that is blocked will only decrease the apparent rate constant, which will ultimately cause peak separation in the CV. For this same reason, as long as the standard rate constant is reasonably large, CV from highly blocked electrodes (with $\delta \gg d_a$ and $\delta \gg d_s$) can look identical to CV from a bare electrode. When the rate constant is lower, the CV becomes quasireversible, and the peak current decreases slightly.

In general, CV and chronoamperometry present difficulties in determining the accessible substrate area due to their dependence on diffusion. However, methods based on measuring the apparent rate constant can yield accurate values. Electrochemical impedance spectroscopy (EIS) can be used to separate the interfacial kinetics from diffusion, solution resistance, and double layer charging currents that may cause inaccuracy. This method has been used to great advantage to examine the fractional surface coverage of self-assembled monolayers. In this method, a small magnitude sinusoidal voltage, V($\omega$), is superimposed on the applied DC potential, set to the formal potential of the redox couple. The current response, I($\omega$), is measured and the complex impedance is calculated via Z($\omega$)=V($\omega$)/I($\omega$) over a broad range of frequencies. If the impedance data can be fit to simple, physically reasonable, equivalent circuits, then the accessible area of a bare or monolayer coated substrate may be accurately determined from the charge transfer resistance. For an electrode coated with a nanoporous film, only the product of the accessible area (A) and the partition coefficient (P) may be determined unambiguously. In the absence of a specific interaction between the redox couple and the silica wall and for pores much larger than the redox couple, P will approach unity. At about pH 2 (where all EIS data were collected in this study), the silica wall is neutral and decorated with hydroxyl groups. As such the partition coefficient is expected to be very close to unity. Further, at about pH=2 hydrolytic degradation of the silica film is negligible, as EIS experiments on the same film immersed for days in the solution yield the same value of the measured accessible area.

Figure 4:
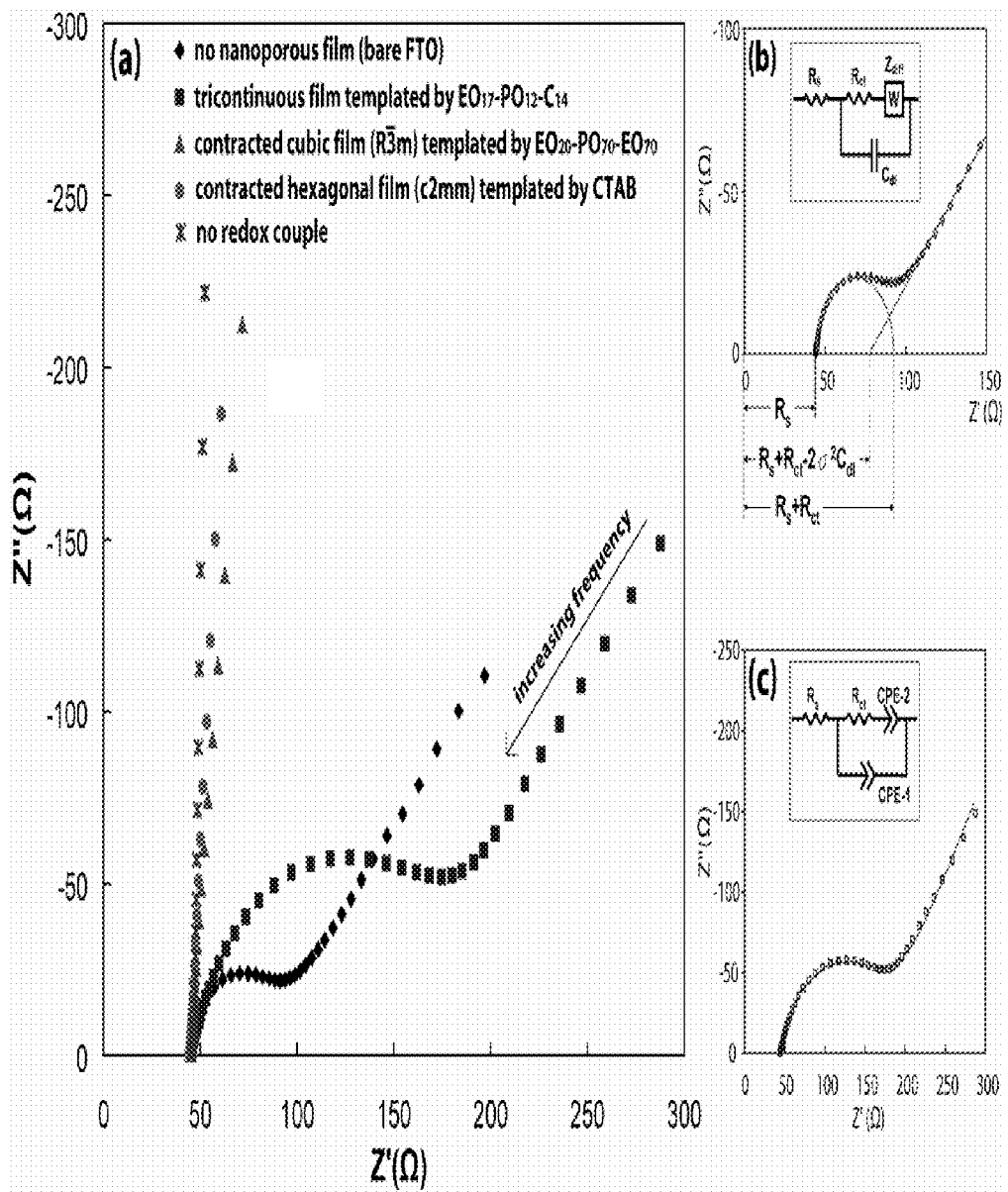
FIG. 4a depicts measured electrochemical impedance data showing that the tricontinuous double-gyroid films yield facile access to the substrate for molecules in solution.
FIG. 4b illustrates how measured electrochemical impedance data relates to the Randles equivalent circuit fit for bare FTO.
FIG. 4c depicts measured electrochemical impedance data of a modified Randles circuit fit for a tricontinuous silica film on FTO.

The EIS data of ferrocene dimethanol on a bare fluorine-doped tin oxide (FTO) electrode fit a Randles equivalent circuit. The charge transfer resistance yielded a value of the standard rate constant of 0.0045 cm/s (using the geometric area of the bare FTO). The measured real and imaginary components of the electrochemical impedance and fitted equivalent circuit models are shown in FIG. 4 as parametric plots as a function of frequency. FTO electrodes coated with crack-free nanoporous silica films show a slightly depressed semicircle in their impedance spectra. This is due to the fact that the double layer at the electrode surface is not a simple planar surface, but extends slightly into the wall structure of the film. Replacing the double layer capacitance ($C_{dl}$) with a constant phase element (CPE) allows one to model this deviation from planarity. The impedance due to a CPE is given by $Z_{CPE}=1/T(j\omega)^p$. The fractional exponent p characterizes the width of the relaxation time distribution due to the inhomogeneity, with p=1 representing a single pure capacitor. The behavior of the diffusion impedance in the mass transfer controlled regime (low frequency) deviates slightly from that expected from Fickian 1D diffusion (an infinite length Warburg element or a CPE with p=0.5). A CPE is used to model this data and yielded a value of p=0.59. However, this element does not affect the value of $R_{ct}$ which is dictated by the higher frequency data where the diffusion impedance is very small.

EIS data were collected from many typical nanoporous films and reveal that highly ordered and oriented contracted 2D hexagonal films and contracted 3D cubic films (rhombohedral space group R-3m) have extremely low accessible substrate areas (less than 0.02%), for the ~6 Å diameter ferrocene dimethanol probe molecule. However, the new tricontinuous films synthesized here have accessible areas of 31%±3%, compared to a bare substrate. The low accessibility in 2D hexagonal films is expected since the mesopores are aligned parallel to the substrate. However, low accessibility in rhombohedral films is surprising, as these films show large nanopore openings in top-view FESEM and are expected to have intercage connections similar to those observed in cubic phase nanoporous silica powders, particularly Fm-3m structures. This lack of accessibility in highly ordered rhombohedral films could be due to the lack of intercage openings or due to the presence of a thin but dense silica layer beneath the nanoporous film. The accessibility increases for hexagonal and rhombohedral films as they become less ordered and less oriented (as the redox couple is able to move through defects and irregular mesopore connections). However, this type of accessibility is qualitatively different for the tricontinuous films reported here, as the accessibility is determined by the regular mesopore structure. This accessible area of the substrate matches amazingly well with footprint the tricontinuous films leaves of the substrate (about 31%) as determined from the structural model derived from GISAXS and TEM (FIG. 3b).

Platinum Nanowire Films with the Double-Gyroid Structure

Figure 5:
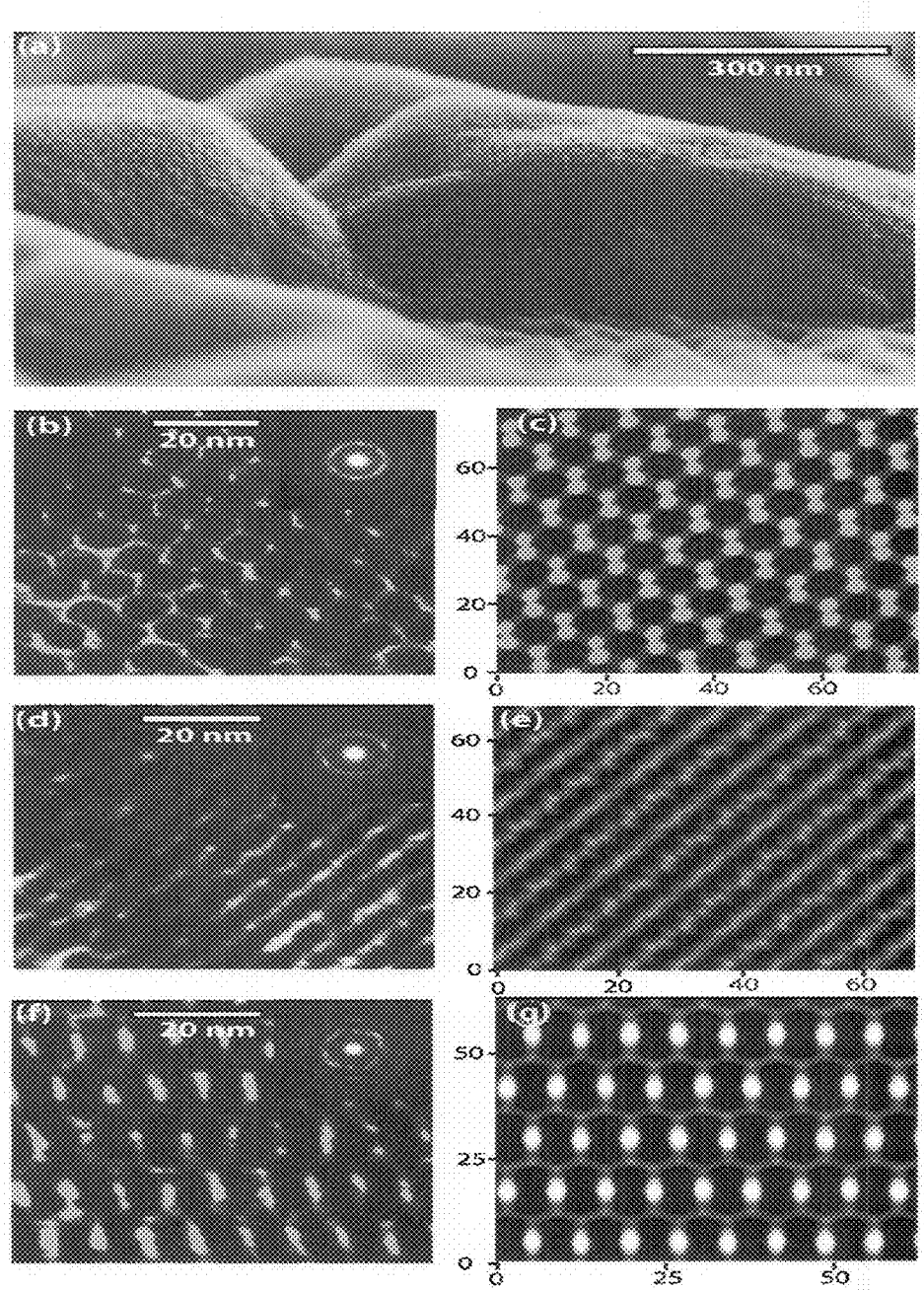
FIGS. 5a-g depict electron microscopy of platinum nanowire structures after the removal of silica.

There are previous reports of electrochemical deposition within nanoporous silica films. However, these were either in contracted 2D hexagonal films with pores parallel to the substrate (meaning the deposition occurred though film defects, regions of nanostructure disorder, or microporosity) or in cage-like cubic structures with irregular pore openings. As a result, none of these electrodeposited structures retain good order after silica removal by etching. The first electrochemical deposition of metals into a true double gyroid-based nanoporous silica film is reported here. The metal fills each of the two continuous pore systems, and due to the pore connectivity and the high pore filling, the nanowire networks are stable to removal of the silica and retain the local and long-range order imposed by the nanopores system of the film. FESEM and TEM micrographs of a platinum nanowire film after removal of the silica by etching in HF are shown in FIG. 5. TEM images were simulated as discussed above, except they were based on a structure where platinum fills the both pore systems and the original silica wall is absent (FIG. 3d). The observed TEM images compare very well with the simulated electron density projections for the [111], [211], and [311] directions.

Figure 6:
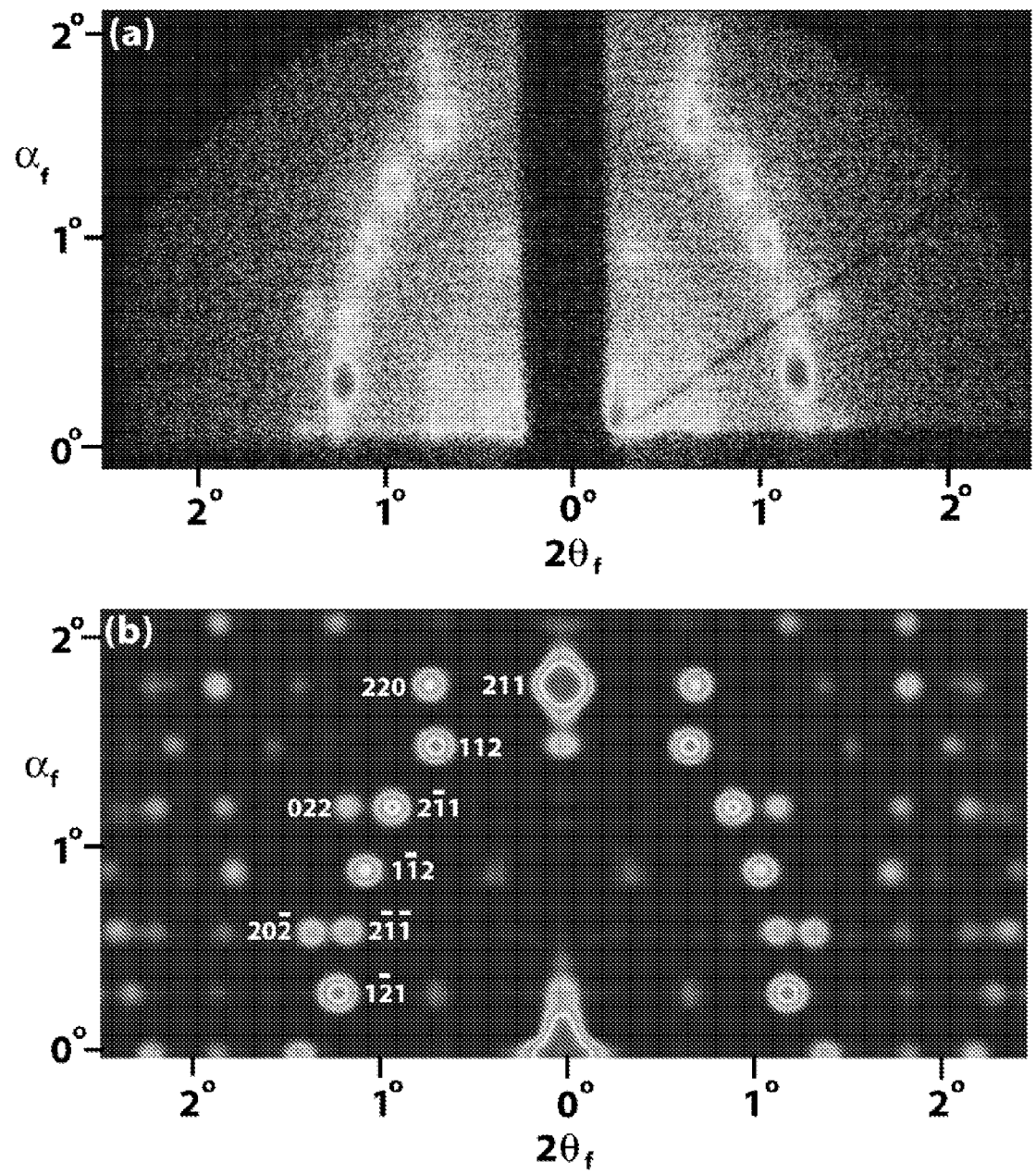
FIG. 6a depicts a measured GISAXS pattern of a platinum nanostructure after silica removal.
FIG. 6b depicts a simulated GISAXS pattern of a platinum nanostructure after silica removal.
Figure 7:
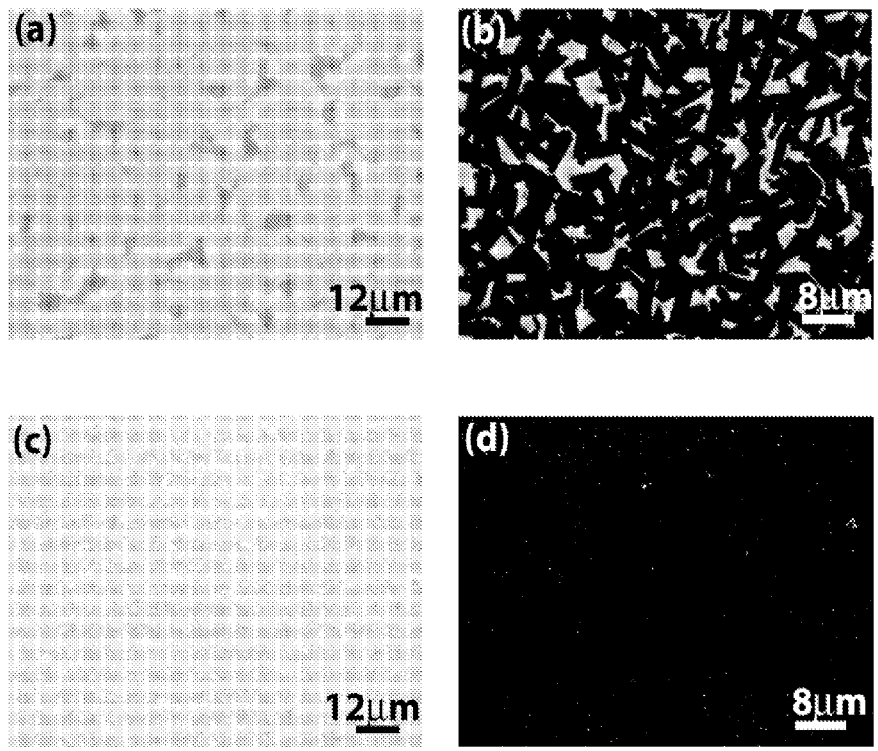
FIGS. 7(a) and 7(c) depict transmission optical micrographs of nanoporous films before electrochemical deposition FIG. 7(b) and (d) depict transmission optical micrographs of films after electrodeposition of cobalt in the pores to form an array of cobalt nanowires
Figure 8:
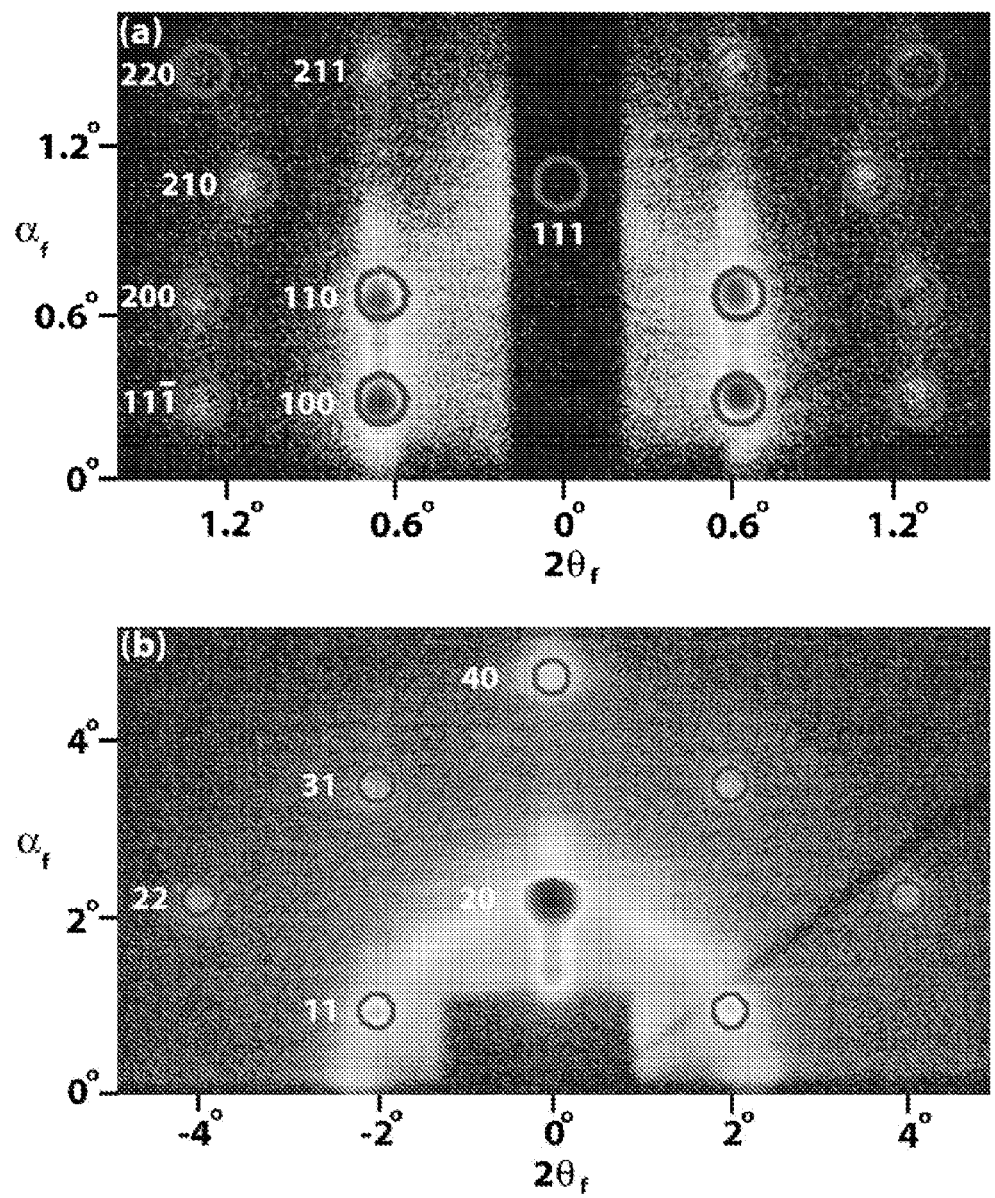
FIG. 8(a)-(b) depict GISAXS patterns of silica films.
Figure 9:
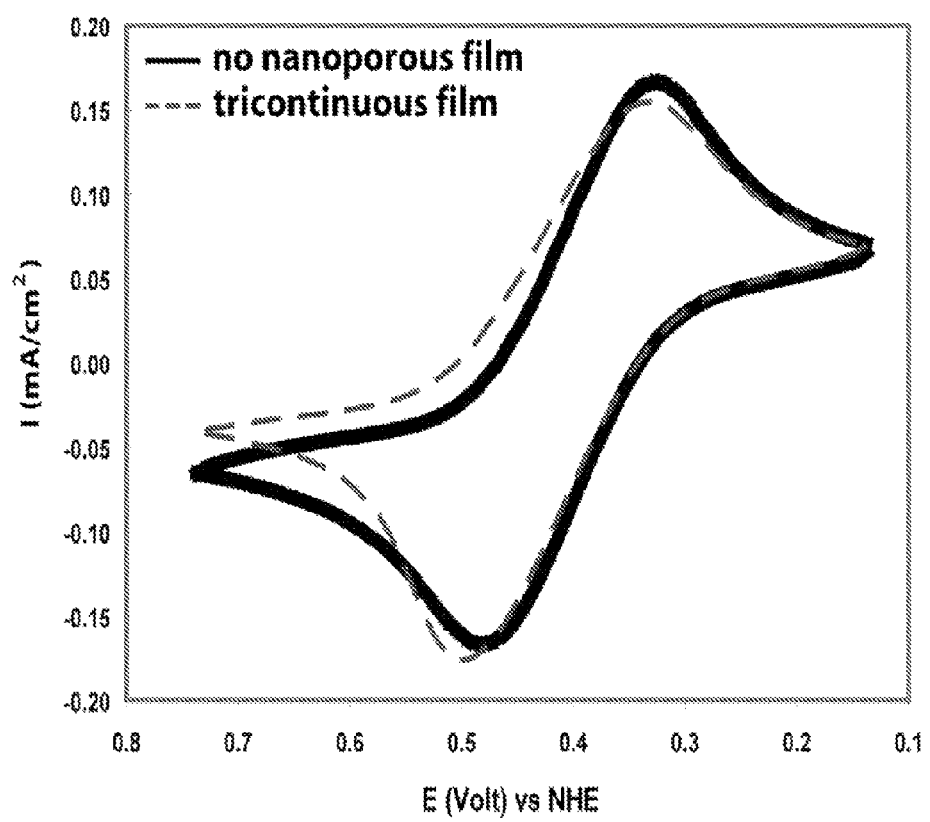
FIG. 9 depicts a cyclic voltammogram of bare FTO and tricontinuous film on FTO.

GISAXS patterns were also collected from the Pt films after silica removal (FIG. 6) and show that long-range order and orientation of the Pt is retained. The observed GISAXS spot pattern and relative intensities match nearly identically to that for the nanoporous silica film (as would be expected by the Babinet Principle). Further, we carried out simulation of the full GISAXS pattern (under the Born Approximation) by taking the discrete Fourier Transform of the Pt nanostructure with the form shown in FIG. 3d. An apodization function (Hanning window) was applied to the data to minimize aliasing effects, and reciprocal space was integrated radially about the [211] axis. The resulting pattern is shown in FIG. 6b. Comparison of the relative peak intensities and peak positions between measured and simulated GISAXS patterns shows that the Pt nanowire network maintains the structure shown in FIG. 3d over large length scales. This also shows that the two continuous nanowire systems (blue and green in FIG. 3d) do not shift relative to one another in contrast to that observed in carbon materials templated by MCM-48. This may be due to the fact that each nanowire network is independently (and regularly) connected to the substrate or perhaps the presence of interconnections such as those observed by Sakamoto.

PbSe Quantum Wire Films with the Double-Gyroid Structure

Following the same procedure as above described for platinum nanowires, wires of other materials may also be grown by electrodeposition in these nanoporous film templates. We have demonstrated this for Pt, Co, Cu, Bi, Bi2Te2, CuInSe2, CdSe, CdTe, PbTe, and PbSe. In FIG. 10, results for PbSe are shown. FIG. 10(a) shows a photograph of a nanoporous silica film that has been filled with PbSe by electrochemical deposition. The photograph shows the macroscopic uniformity of the films and the high fill fraction of PbSe. The films shown in FIG. 10(a) is composed of about 4 nm wires of PbSe. For this material, these are not just uniform nanowires (which are wires of uniform diameter less than about 100 nm), but they are quantum wires. The small diameter of the wires and the uniform structure provided by the double-gyroid topology results in quantum confinement of electrons in the PbSe. The is shown in reflectivity data shown in FIG. 10(b). The oscillations in the reflectivity are due to spikes in the density of states due to quantum confinement. This is a key discovery since it is believed that quantum confinement is a key and necessary feature for enhanced efficiency photovoltaics devices and thermoelectric devices. In our studies we have been able to make sub 5 nm wires from any metal or semiconductor we have tried. These results prove the general utility of the present teachings for making small diameter nanowire or quantum wire arrays.

Methods

Synthesis of NanoDorous Silica Films

For tricontinuous silica films from TEOS and $EO_{17}$-$PO_{12}$-$C_{14}$, tetraethyl orthosilicate (TEOS) was prehydrolyzed at room temperature. About 6.35 g of about a pH 1.76 solution of HCl in water was added to about 12.86 g of ethanol in an HDPE bottle. About 12.2 g of TEOS was then added quickly. The bottle was immediately sealed and stirred for about 20 minutes at about 21° C. The prehydrolysis solution had a molar ratio of 1 TEOS: 0.0019HCl: 6.0 $H_2O$: 4.8 EtOH. Immediately after prehydrolysis, about 13.9 g of about 37 wt % $EO_{17}$-$PO_{12}$-$C_{14}$ in ethanol was added to form the coating solution. The coating solution was then aged for different times at about 21° C. The final molar composition of the coating solution was 1 TEOS: 0.054 $EO_{17}$-$PO_{12}$-$C_{14}$: 0.0019HCl: 6.0 $H_2O$: 8.0 EtOH. Before coating, fluorine-doped $SnO_2$ (FTO) substrates were cleaned by immersion in about 1 wt % Alconox at about 65° C. for about 30 seconds followed by rinsing with copious quantities of RO water and air dried. Films were dip-coated on FTO using this solution at a withdrawal speed of 1 mm/sec. High quality films were formed after dip-coating at about 40% relative humidity (RH) after about 10 days of aging of the coating solution. After coating, films were left at the same RH for about 12 hrs and then calcined in air at about 400° C. for about 4 hours (with about 1° C./min ramps). Contracted 2D hexagonal films (plane group c2 mm) were synthesized as published by Cagnol, and contracted face-centered cubic films (rhombohedral space group R-3m) were synthesized as published previously.

For tricontinuous silica films from TEOS and $EO_{19}$-$PO_{43}$-$EO_{19}$, the $EO_{19}$-$PO_{43}$-$EO_{19}$ (P84) surfactant was received as a gift from BASF and was used as-received. The nominal molecular weight of Pluronic-P84 is 4200 and its EO content is approximately 40%. Tetraethyl orthosilicate (TEOS, 98% w/w, Aldrich) was used as the silica precursor. Concentrated (37% w/w) hydrochloric acid was purchased from Aldrich and ethyl alcohol (>99.5%) from EMD Chemicals. All chemicals were ACS reagent grade and were used as-received. The coating solution is prepared by mixing a pre-hydrolyzed silicate solution with an ethanolic surfactant solution. Specifically, about 5.49 g of Pluronic-P84 was dissolved in about 14 g of ethyl alcohol and was allowed to equilibrate overnight at about 21° C. with vigorous stirring. TEOS was pre-hydrolyzed at room temperature (about 21° C.). About 6.35 g of about 0.017 M hydrochloric (pH ~1.8) was mixed with about 12.9 g of ethyl alcohol in an HDPE bottle. To this solution, about 12.19 g of TEOS was added and the bottle was sealed. The solution was stirred vigorously at about 21° C. for about 20 min. The molar composition of the pre-hydrolysis solution was: TEOS:HCl:$H_2O$:EtOH=1:0.0019:6.0:4.8. After the pre-hydrolysis step, the surfactant solution was mixed with the pre-hydrolyzed silicate solution and stirred vigorously at room temperature for about 10 min. This mixed solution, termed as 'coating solution', was afterwards allowed to age at room temperature without stirring. The molar composition of the coating solution was: TEOS:P84:HCl:$H_2O$:EtOH=1:0.02229:0.0019:6.0:10. Periodically, thin films were prepared from the coating solution by a dip-coating process at different aging times. The substrates, fluorine-doped tin oxide (FTO) slides with sheet resistance of 8 Ω/sq, were cleaned by immersing in a boiling, about 2% (w/w) solution of Alconox laboratory detergent for about 5 min, followed by rinsing in RO water to remove traces of detergent. Then they were immersed in a solution consisting of about 70% (w/w) nitric acid and 37% (w/w) hydrochloric acid in 1:3 weight ratio ('aqua-regia') for 20 min at 21° C., followed by a rinse in RO water. The FTO substrates were then dried in a stream of clean, dry air and were used immediately for dip-coating. Silica films were dip-coated on the substrates at a withdrawal speed of about 1 mm/sec under controlled relative humidity of about 40% at room temperature (about 21° C.). These are the same coating conditions we used previously with $EO_{17}$-$PO_{12}$-$C_{14}$/silica system. The films were left at the same relative humidity overnight, before being calcined at about 450° C. for about 4 hours in air with a ramp of about 2° C./min. Double-gyroid silica films are obtained this solution after aging for only about 6 hours and can be made beyond about 3 days of aging.

Determination of Accessible Area of the Substrate

A standard three-electrode cell was used for all experiments with the calcined nanoporous film coated FTO as the working electrode (about 1.5 $cm^2$ geometric area submersed), a platinum counter electrode with about 20 $cm^2$, and a Ag/AgCl reference electrode. The electrolyte contained 1 mM 1,1'-ferrocenedimethanol redox couple, 1M KCl supporting electrolyte, and 0.01 M HCl such that the pH≈2. The formal potential was determined by cyclic voltammetry using a PAR 283 potentiostat to be 0.21 V vs Ag/AgCl. Electrochemical impedance spectroscopy data were then collected using a Solartron 1260 with a DC bias set to the measured formal potential with an AC bias of magnitude 10 mV (rms). These data were collected over a frequency range from about 0.1 Hz to 0.1 MHz. The data were fit by complex non-linear least squares to either a Randles equivalent circuit or a modified Randles circuit with constant phase elements substituted for the double layer capacitance or the Warburg element. The accessible area was then calculated from the charge transfer resistance for the one-electron reaction given by: $R_{ct}$=RT/$F^2$kAPC, where k is the standard rate constant, A the accessible substrate area, P the partition coefficient of the redox couple in the film, C the bulk concentration of the redox couple, and F is the Faraday constant. k was determined by EIS on a bare electrode under identical conditions.

Electrodeposition of Nanowire Networks in Nanoporous Silica Films

The same three electrode cell as above was used for potentiostatic depositions. The working electrode (nanoporous film coated FTO) was immersed into a deoxygenated electrolyte solution for ten minutes prior to deposition. For platinum nanowires the electrolyte was about 0.022M hexachloroplatinic acid ($H_2PtCl_6$) in RO water (pH=1.5), and the depositions were carried out at a constant potential of −0.3V vs. Ag/AgCl at about 21° C. until the current integrated to 1.5 $C/cm^2$. The silica was then removed by etching the film in about a 2 wt % HF solution for about 4 hours at about 21° C. For PbSe quantum wire films the electrodeposition bath contained about 0.1 M $Pb(NO_3)_2$ and 0.001 M $SeO_2$ dissolved in about a 0.1 M $HNO_3$ aqueous solution. Prior to electrodeposition, nitrogen or argon gas was bubbled through the solution for 10 min. The electrochemical cell contained a double-gyroid silica coated FTO as working electrode, a Pt wire as counter electrode and an Ag/AgCl in about 4 M KCl reference electrode. Stoichiometric PbSe films could be deposited from this bath under potentiostatic conditions over a potential range of about −0.20 V to −0.40 V versus the Ag/AgCl electrode. Unless otherwise stated, all films reported in this work were deposited at about −0.30V versus the Ag/AgCl electrode. The thickness of deposited PbSe could be controlled by controlling the amount of charge passed. ~300 nm thick PbSe/silica nanocomposite film was created by passing a charge of about 0.27 $C/cm^2$ of substrate area. The films were rinsed in RO water after deposition and allowed to dry in air. While as deposited PbSe films were crystalline, a thermal treatment in flowing nitrogen at about 500° C. was done to improve structural strength of the PbSe nanowire network embedded in silica. The silica template was then removed by etching in freshly prepared 1 M KOH for about 30 min.

Reflectivity Measurements

The Reflectivity measurements were done on bulk and double-gyroid PbSe films using Analytical Spectral Devices, Inc. FieldSpec® 3 portable spectroradiometer. The spectral range for this instrument is 350 nm-2500 nm, corresponding to an energy range from about 3.54 eV-0.50 eV. The probe was mounted directly on the thin film to measure the reflectance from the film. The film was artificially illuminated by an external broadband direct current light source with reflectance measured on 2151 channels. Prior to doing measurements on actual films, the instrument was calibrated using Labsphere Spectralon® white reflectance material. The instrument was set to measure the reflectance from the PbSe film (not radiance, which would include contributions from the source lamp).

Further description of the present invention may be found in "Nanofabrication of Double-Gyroid Thin Films," Journal of the American Chemical Society, Vol. 19, No. 4, pp 768-777 (2007), Vikrant N. Urade et al., see Appendix A; "Controlling Interfacial Curvature in Nanoporous Silica Films Formed by Evaporation-Induced Self-Assembly from Nonionic Surfactants. I. Evolution of Nanoscale Structure in Coating Solutions," Journal of the American Chemical Society, Vol. 23, No. 8, pp 4257-4267 (2007), Luis Bollmann et al., see Appendix B; "Controlling Interfacial Curvature in Nanoporous Silica Films Formed by Evaporation-Induced Self-Assembly from Nonionic Surfactants. II. Effect of Processing Parameters on Film Structure," Journal of the American Chemical Society, Vol. 23, No. 8, pp 4268-4278 (2007), Vikrant N. Urade et al., see Appendix C; and "Mass Transport and Electrode Accessibility Through Periodic Self-Assembled Nanoporous Silica Thin Films," Journal of the American Chemical Society, Vol. 23, No. 10, pp 5689-5699 (2007), Ta-Chen Wei et al., see Appendix D, the entire contents of each are incorporated herein by reference.

While an exemplary embodiment incorporating the principles of the present invention has been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

The invention claimed is:

1. A method of forming a nanoporous film, the method comprising:
    forming a coating solution including clusters, surfactant molecules, a solvent, and one of an acid catalyst and a base catalyst, the clusters comprising inorganic groups;
    aging the coating solution for a time period to select a predetermined phase that will self-assemble;
    applying the coating solution on a substrate;
    evaporating the solvent from the coating solution;
    removing the surfactant molecules to yield the nanoporous film; and
    controlling one or a plurality of a water concentration in the coating solution, a pH of the coating solution, a temperature and a time of aging the coating solution, a relative humidity during coating, and a vapor phase composition after coating;
        wherein the clusters are formed from hydrolysis of one of a silicon alkoxide comprising tetraethylorthosilicate and a silicon halide of a form $SiX_4$, wherein X comprises fluorine, chlorine, bromine, iodine, astatine, or combinations thereof; and
        wherein the surfactant molecules comprise a poly(ethylene oxide)-poly(propylene oxide)-alkane copolymer with the formula $H(OCH_2CH_2)_{17}-(OCH(CH_3)CH_2)_{12}-(CH_2)_{13}CH_3$.

2. The method of claim 1 wherein the clusters comprise silicon and oxygen to yield a nanoporous film having walls comprising silicon and oxygen.

3. The method of claim 1 wherein the clusters comprise silicon, carbon, and oxygen to yield a nanoporous film having walls comprising silicon, carbon, and oxygen.

4. The method of claim 1 wherein the time period is sufficient to select the desired nanostructured film that will self-assemble after coating from one of the following periodic self-assembled phases: face-centered cubic, body-centered cubic, primitive cubic, rhombohedral, orthorhombic, Pm-3n cubic, Pn-3m cubic, three-dimensional hexagonal, two-dimensional hexagonal, two-dimensional rectangular, disordered wormhole, double-gyroid, L3 sponge phase, or the lamellar phase.

5. The method of claim 1 wherein the time period decreases the interfacial curvature.

6. The method of claim 1 wherein the time period corresponds to a double gyroid-based structure of the nanoporous film.

7. A method of forming a nanoporous film, the method comprising:
    forming a coating solution including clusters, surfactant molecules, a solvent, and one of an acid catalyst and a base catalyst, the clusters comprising inorganic groups;
    aging the coating solution for a time period to select a predetermined phase that will self-assemble;
    applying the coating solution on a substrate;
    evaporating the solvent from the coating solution;
    removing the surfactant molecules to yield the nanoporous film; and
    controlling one or a plurality of a water concentration in the coating solution, a pH of the coating solution, a temperature and a time of aging the coating solution, a relative humidity during coating, and a vapor phase composition after coating;
        wherein the clusters are formed from hydrolysis of one of a silicon alkoxide comprising tetraethylorthosilicate and a silicon halide of a form $SiX_4$, wherein X comprises fluorine, chlorine, bromine, iodine, astatine, or combinations thereof; and
        wherein the surfactant comprises a poly(ethylene oxide)-poly(propylene oxide)-poly(ethylene oxide) copolymer with the formula $H(OCH_2CH_2)_{19}-(OCH(CH_3)CH_2)_{43}-(OCH_2CH_2)_{19}H$.

8. The method of claim 7 wherein the clusters comprise silicon and oxygen to yield a nanoporous film having walls comprising silicon and oxygen.

9. The method of claim 7 wherein the clusters comprise silicon, carbon, and oxygen to yield a nanoporous film having walls comprising silicon, carbon, and oxygen.

10. The method of claim 7 wherein the time period is sufficient to select the desired nanostructured film that will self-assemble after coating from one of the following periodic self-assembled phases: face-centered cubic, body-centered cubic, primitive cubic, rhombohedral, orthorhombic, Pm-3n cubic, Pn-3m cubic, three-dimensional hexagonal, two-dimensional hexagonal, two-dimensional rectangular, disordered wormhole, double-gyroid, L3 sponge phase, or the lamellar phase.

11. The method of claim 7 wherein the time period decreases the interfacial curvature.

12. The method of claim 7 wherein the time period corresponds to a double gyroid-based structure of the nanoporous film.

* * * * *